(12) United States Patent
Naito

(10) Patent No.: US 6,699,376 B2
(45) Date of Patent: Mar. 2, 2004

(54) GAS SENSING ELEMENT AND GAS SENSOR

(75) Inventor: Susumu Naito, Kariya (JP)

(73) Assignee: Denso Corporation (JP)

( * ) Notice: Subject to any disclaimer, the term of this patent is extended or adjusted under 35 U.S.C. 154(b) by 16 days.

(21) Appl. No.: 09/993,695

(22) Filed: Nov. 27, 2001

(65) Prior Publication Data

US 2002/0070110 A1 Jun. 13, 2002

(30) Foreign Application Priority Data

Dec. 7, 2000 (JP) .......................................... 2000-373422

(51) Int. Cl.[7] .............................................. G01N 27/407
(52) U.S. Cl. ........................ 204/429; 204/425; 204/426; 204/427; 204/428
(58) Field of Search ................................. 204/421–429

(56) References Cited

U.S. PATENT DOCUMENTS

| | | | | |
|---|---|---|---|---|
| 3,088,905 A | * | 5/1963 | Glover | |
| 4,097,353 A | * | 6/1978 | Kishida et al. | |
| 4,116,797 A | * | 9/1978 | Akatsuka | |
| 4,174,258 A | * | 11/1979 | Bode | |
| 4,233,142 A | * | 11/1980 | Rohr et al. | |
| 4,655,901 A | * | 4/1987 | Mase et al. | |
| 4,741,817 A | * | 5/1988 | Croset et al. | |
| 4,879,016 A | * | 11/1989 | Joshi | |
| 5,695,625 A | * | 12/1997 | Yamada et al. | |
| 6,036,841 A | * | 3/2000 | Kato et al. | |

FOREIGN PATENT DOCUMENTS

JP 2000-55854 2/2000

* cited by examiner

Primary Examiner—T. Tung
(74) Attorney, Agent, or Firm—Nixon & Vanderhye PC

(57) ABSTRACT

A measured gas side electrode is provided on one surface of a solid electrolytic substrate so as to be exposed to a measured gas. A reference gas side electrode is provided on an opposite surface of the solid electrolytic substrate so as to be exposed to a reference gas stored in a reference gas chamber. A water-vapor absorbing member is provided in the reference gas chamber.

1 Claim, 8 Drawing Sheets

GAS SENSING ELEMENT AND GAS SENSOR

BACKGROUND OF THE INVENTION

The present invention relates to a gas sensing element and a gas sensor used for controlling the combustion of an internal combustion engine.

Conventionally, a gas sensor is equipped in an exhaust gas system of an automotive vehicle to control an air-fuel ratio of gas mixture introduced into an internal combustion engine.

A gas sensing element, disposed in the gas sensor, usually comprises a solid electrolytic substrate having oxygen ion conductivity, a measured gas side electrode provided on the solid electrolytic substrate so as to be exposed to a measured gas, and a reference gas side electrode provided on the solid electrolytic substrate so as to be exposed to a reference gas.

The gas sensing element obtains a sensing value (e.g., limit current value) representing the concentration of oxygen involved in exhaust gas. The sensing value of the gas sensing element reflects the air-fuel ratio in a combustion chamber of an internal combustion engine.

The internal combustion engine is often left in an inoperative condition for a long time (e.g., several hours and several days). It is conventionally known that the gas sensing element produces an extraordinary output at a moment the engine is operated again after such a long interruption.

This kind of extraordinary sensor output continues for several seconds to several tens seconds after a cold starting up of the engine. During this period, the sensor output shifts with a great extent to the rich side (refer to a later-described characteristic curve (c) shown in FIG. 4).

In response to such an abnormal sensor output (i.e., an extraordinary rich signal), an engine control system adjusts an air-fuel ratio of the gas mixture introduced into the combustion chamber to a lean side.

However, the detected extraordinary rich signal does not reflect an actual air-fuel condition in the combustion chamber. Continuously generating a lean signal during a significant period will result in an excessive increase of oxygen in the combustion chamber. The fuel amount reduces contrarily and will stop the engine due to the shortage of fuel.

The occurrence of such an extraordinary sensor output is generally limited to a first startup operation when the engine is driven after a long-term interruption. Such a problem is no longer found in the second or succeeding startup operations.

SUMMARY OF THE INVENTION

To solve the above-described problems, an object of the present invention is to provide a gas sensing element and a gas sensor capable of accurately detecting the oxygen concentration as well as the air-fuel ratio even after the engine is left in an inoperative condition for a long time.

In order to accomplish the above and other related objects, the present invention provides a first gas sensing element comprising a solid electrolytic substrate. A measured gas side electrode is provided on one surface of the solid electrolytic substrate so as to be exposed to a measured gas. A reference gas side electrode is provided on an opposite surface of the solid electrolytic substrate so as to be exposed to a reference gas stored in a reference gas chamber. And, a water-vapor absorbing member is provided in the reference gas chamber.

The first gas sensing element of this invention is characterized in that the water-vapor absorbing member is provided in the reference gas chamber.

The water-vapor absorbing member is any substance capable of trapping water components and is not limited to a specific material. Details of the water-vapor absorbing member will be explained later.

The first gas sensing element of this invention operates in the following manner.

First of all, it is believed that the abnormal sensor output is produced according to the following mechanism.

The gas sensing element, after being left for a long time (several hours or several days), produces an abnormal sensor output. The magnitude of the abnormal sensor output is dependent on the humidity of an atmosphere in which the gas sensing element is left.

The inventor of the present invention has heated a gas sensing element being left for a long term to check the component of a gas leaving out of this gas sensing element and detected a great amount of $H_2O$ adhering on the gas sensing element.

Namely, when a gas sensing element is left in an atmosphere including moisture, water molecules adhere or settle on a reference gas side electrode. The largeness of an abnormal sensor output shows the presence of a great amount of water molecules. It is believed that a large surface roughness of the reference gas electrode allows the water molecules to easily adhere or settle on the surface of the reference gas side electrode. Once the water molecules adhere or settle on the electrode surface, another water molecules easily accumulate thereon through hydrogen bridge.

The gas sensing element in such condition is subjected to heat upon starting the operation of the engine.

As shown in FIG. 2, the supply of heat and the catalytic function of a reference gas side electrode 112 cooperatively activate the water molecules adhering on the surface of a solid electrolytic substrate 12 and decompose them into oxygen atoms and hydrogen atoms. Oxygen atoms, when ionized, move toward a measured gas side electrode 111 across the solid electrolytic substrate 12 as an oxygen ion current. The oxygen ion current thus produced is believed to cause an abnormal sensor output.

Once all of the water molecules have decomposed, no abnormal sensor output is produced. Hence, no problem occurs in the second and succeeding startup operations of the engine as long as no water molecules remain on the surface of the reference gas side electrode.

In view of the above, the present invention provides the water-vapor absorbing member in the reference gas chamber to prevent the water molecules from adhering on the surface of the reference gas side electrode. Thus, it becomes possible to obtain an accurate sensor output reflecting an actual oxygen concentration in the measured gas.

As apparent from the foregoing description, the present invention provides an excellent gas sensing element capable of accurately detecting the oxygen concentration as well as the air-fuel ratio even after the engine is left in an inoperative condition for a long time.

According to a preferable embodiment of the present invention, the water-vapor absorbing member is provided so as to close an inside space of the reference gas chamber.

This arrangement makes it possible to prevent the water vapor from entering into the reference gas chamber.

The water-vapor absorbing member can be provided at an opening end of the reference gas chamber so as to close the opening end entirely as shown in FIG. 1. In general, the opening end of the reference gas chamber is a place where the temperature is not so increased. Thus, a member not strong against heat can be used as the water-vapor absorbing member.

Furthermore, as shown in FIG. 3, it is possible to provide the water-vapor absorbing member at an intermediate position so as to close a middle part of the reference gas chamber. This arrangement is advantageous in that the water-vapor absorbing member is free from damage when the gas sensing element is installed in a gas sensor.

In any case, it is preferable to the water-vapor absorbing member is disposed entirely along the inside wall of the reference gas chamber so as to prevent the water vapor from reaching the reference gas side electrode.

According to the preferable embodiment of the present invention, the water-vapor absorbing member is provided so as to cover the reference gas side electrode provided in the reference gas chamber (refer to FIG. 5).

This arrangement surely prevents the water molecules from reaching the reference gas side electrode.

According to the preferable embodiment of the present invention, the water-vapor absorbing member is porous.

When the water vapor passes through the porous member, the water vapor collides with a wall surface of a labyrinth formed in this porous member. The wall surface absorbs (i.e., traps) the water vapor and accordingly prevents the water molecules from reaching the reference gas side electrode.

According to the preferable embodiment of the present invention, the water-vapor absorbing member is a porous alumina.

Due to excellent heat durability of alumina, it becomes possible to prevent the gas sensing element from deteriorating when exposed to high-temperature exhaust gas.

Especially, the water-vapor absorbing member made of a porous alumina will show excellent durability when the water-vapor absorbing member is disposed closely to a high-temperature portion (e.g., the reference gas side electrode).

Besides porous alumina, activated charcoal and silica gel are substances preferable for the water-vapor absorbing member. Although its heat durability is not so excellent, the activated charcoal is inexpensive and therefore can be used as a water-vapor absorbing member provided in the vicinity of the opening end of the reference gas chamber. Although its absorbing ability is not so good compared with activated charcoal, silica gel is stable in a high-temperature atmosphere and can be used as a water-vapor absorbing member provided closely to a high-temperature portion.

It is also preferable to use a water-vapor absorbing member made of a porous ceramic.

The present invention provides a gas sensor having a gas sensing element comprising a solid electrolytic substrate, a measured gas side electrode provided on one surface of the solid electrolytic substrate so as to be exposed to a measured gas, and a reference gas side electrode provided on an opposite surface of the solid electrolytic substrate so as to be exposed to a reference gas stored in a reference gas chamber. The gas sensor of the present invention is characterized by a cylindrical housing for securely holding the gas sensing element, a reference gas side cover provided at a proximal end side of the housing and having an air introducing hole, a measured gas side cover provided at a distal end side of the housing, and a water-vapor shielding portion or a water-vapor absorbing member provided in an air introducing passage extending from the air introducing hole to the reference gas chamber (refer to FIG. 6).

According to the gas sensor of the present invention, the air entering from the air introducing hole is introduced into the reference gas chamber in the gas sensing element. The water-vapor shielding portion or the water-vapor absorbing member, provided in an air introducing passage, prevents the water vapor from entering into the reference gas chamber.

Accordingly, it becomes possible to surely prevent the water molecules from entering into the reference gas chamber even when the gas sensing element is left in an inoperative condition for a long time.

As apparent from the foregoing description, the present invention provides an excellent gas sensor capable of accurately detecting the oxygen concentration as well as the air-fuel ratio even after the engine is left in an inoperative condition for a long time.

According to the preferable embodiment of the present invention, the water-vapor shielding portion is a cover member capable of selectively opening or closing the air introducing passage.

This arrangement is advantageous in that no processing to the reference gas chamber is required. In other words, the present invention provides a gas sensor which is easy to manufacture.

It is preferable that the cover member opens the air introducing passage upon starting the operation of the engine and closes the air introducing passage upon stopping the operation of the engine. Regarding an opening/closing mechanism for the cover member, it is possible to utilize a motor, a servo mechanism, an other actuator as well as a bimetal and a shape memory alloy.

According to the preferable embodiment of the present invention, the water-vapor absorbing member is porous.

When the water vapor passes through the porous member, the water vapor colliders with a wall surface of a labyrinth formed in this porous member. The wall surface absorbs (i.e., traps) the water vapor and accordingly prevents the water molecules from reaching the reference gas side electrode.

According to the preferable embodiment of the present invention, the reference gas chamber of the gas sensing element has an opening end communicating with an inside space of the reference gas side cover, and the water-vapor shielding portion or the water-vapor absorbing member is provided at the opening end of the reference gas chamber.

With this arrangement, it becomes possible to effectively prevent the water vapor from entering into the reference gas chamber.

The present invention provides a second gas sensing element comprising a solid electrolytic substrate, a measured gas side electrode provided on one surface of the solid electrolytic substrate so as to be exposed to a measured gas, and a reference gas side electrode provided on an opposite surface of the solid electrolytic substrate so as to be exposed to a reference gas stored in a reference gas chamber, characterized in that an insulating thin film is provided on a surface of the reference gas side electrode.

According to the second gas sensing element of the present invention, the water molecules adhering or settling on the electrode surface is blocked by the insulating thin film and cannot reach the reference gas side electrode. Due to its kinetic energy, the oxygen residing in the reference gas chamber can penetrate through the insulating thin film. Accordingly, the insulating thin film does not give any adverse influence to the performance of the gas sensing element. The second gas sensing element of the present invention can effectively eliminate an abnormal sensor output caused by an oxygen ion current derived from water molecules.

As apparent from the foregoing description, the present invention provides an excellent gas sensing element capable of accurately detecting the oxygen concentration as well as the air-fuel ratio even after the engine is left in an inoperative condition for a long time.

According to the preferable embodiment of the present invention, a thickness of the insulating thin film is in a range from 1 nm to 10 nm.

This arrangement surely prevents the water molecules from decomposing on the reference gas side electrode.

If the thickness of the insulating thin film is less than 1 nm, it will be difficult to obtain the effects of the present invention. If the thickness of the insulating thin film exceeds 10 nm, the electrode will obtain inappropriate insulating ability and therefore the sensor performance will go worse.

The present invention provides a third gas sensing element comprising a solid electrolytic substrate, a measured gas side electrode provided on one surface of the solid electrolytic substrate so as to be exposed to a measured gas, and a reference gas side electrode provided on an opposite surface of the solid electrolytic substrate so as to be exposed to a reference gas stored in a reference gas chamber, characterized in that a surface roughness of the reference gas side electrode is 3 $\mu$m at maximum.

This arrangement substantially smoothens the electrode surface, thereby reducing the water molecules adhering or settling on the electrode surface. Thus, the third gas sensing element of the present invention can effectively eliminate an abnormal sensor output caused by an oxygen ion current derived from water molecules.

If the surface roughness of the reference gas side electrode is larger than 3 $\mu$m, the magnitude of an abnormal sensor output will become so large that it cannot be handled as an allowable error. The maximum surface roughness, measurable with a surface roughness meter, is a value defined as a difference between a highest position and a lowest position on a measured surface.

As apparent from the foregoing description, the present invention provides an excellent gas sensing element capable of accurately detecting the oxygen concentration as well as the air-fuel ratio even after the engine is left in an inoperative condition for a long time.

The present invention provides a first method for manufacturing a gas sensing element comprising a solid electrolytic substrate, a measured gas side electrode provided on one surface of the solid electrolytic substrate so as to be exposed to a measured gas, and a reference gas side electrode provided on an opposite surface of the solid electrolytic substrate so as to be exposed to a reference gas stored in a reference gas chamber. The first manufacturing method of the present invention comprises the steps of preparing a first green sheet for forming the solid electrolytic substrate and a second green sheet for forming the reference gas chamber, providing a first print portion on the first green sheet to form the measured gas side electrode and a second print portion to form the reference gas side electrode, applying a pressing force on the first green sheet, laminating the first and second green sheets integrally, pressing the first and second green sheets together to obtain a pressed lamination body, and sintering the pressed lamination body. The first manufacturing method of the present invention is characterized in that the pressing force applied on the first green sheet is in a range from 10 MPa to 70 MPa.

By applying the pressing force of 10 MPa to 70 MPa on the solid electrolytic green sheet, it becomes possible to obtain a reference gas side electrode having a smooth surface. Accordingly, water molecules cannot easily adhere or settle on the reference gas side electrode. Thus, it becomes possible to obtain a gas sensing element capable of effectively eliminating an abnormal sensor output caused by an oxygen ion current derived from water molecules.

If the pressing force is less than 10 MPa, it will be difficult to obtain an effect of this invention. If the pressing force exceeds 70 MPa, a significant damage will be given to the green sheet and a cracking will be produced during the sintering process.

As apparent from the foregoing description, the present invention provides an excellent manufacturing method for a gas sensing element capable of accurately detecting the oxygen concentration as well as the air-fuel ratio even after the engine is left in an inoperative condition for a long time.

The present invention provides a second method for manufacturing a gas sensing element comprising a solid electrolytic substrate, a measured gas side electrode provided on one surface of the solid electrolytic substrate so as to be exposed to a measured gas, and a reference gas side electrode provided on an opposite surface of the solid electrolytic substrate so as to be exposed to a reference gas stored in a reference gas chamber. The second manufacturing method of the present invention comprises the steps of preparing a first green sheet for forming the solid electrolytic substrate and a second green sheet for forming the reference gas chamber, providing a first print portion on the first green sheet to form the measured gas side electrode and a second print portion to form the reference gas side electrode, laminating the first and second green sheets integrally and pressing the first and second green sheets together to obtain a pressed lamination body, and sintering the pressed lamination body. The second manufacturing method of the present invention is characterized in that the second print portion for forming the reference gas side electrode includes 5–10 wt % $ZrO_2$ grains contained in 100 wt % electrode paste.

Mixing $ZrO_2$ grains with a paste of the reference gas side electrode makes it possible to improve the adherence between the solid electrolytic substrate and the reference gas side electrode because $ZrO_2$ grains can integrate with the solid electrolytic substrate during the sintering operation. However, $ZrO_2$ grains possibly increase the surface roughness of the solid electrolytic substrate. Accordingly, the reference gas side electrode will have a surface reflecting the increased surface roughness of the solid electrolytic substrate.

Hence, in forming the print part of the reference gas side electrode, using the above-described electrode paste makes it possible to effectively reduce the surface roughness of the reference gas side electrode without being adversely influenced by the inclusion of $ZrO_2$ grains. Accordingly, the surface of the reference gas side electrode becomes so smooth that molecules cannot easily adhere or settle on the reference gas side electrode. It becomes possible to obtain a gas sensing element capable of effectively eliminating an abnormal sensor output caused by an oxygen ion current derived from water molecules.

If the percentage of $ZrO_2$ grains is less than 5 wt %, the adherence between the solid electrolytic substrate and the reference gas side electrode will deteriorate and cause them to easily peel off. If the percentage of $ZrO_2$ grains is larger than 10 wt %, it will be difficult to obtain an effect of this invention.

As apparent from the foregoing description, the present invention provides an excellent manufacturing method for a gas sensing element capable of accurately detecting the oxygen concentration as well as the air-fuel ratio even after the engine is left in an inoperative condition for a long time.

The electrode paste can include various binders in addition to the electrode materials.

The application of the present invention is not limited to a one-cell type gas sensing element (i.e., comprising a pair of electrodes formed on opposed surfaces of a solid electrolytic substrate as shown in FIG. 1). Therefore, the present invention can be preferably applied to a two-cell type gas sensing element as shown in a later-described seventh embodiment.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

Figure 1:
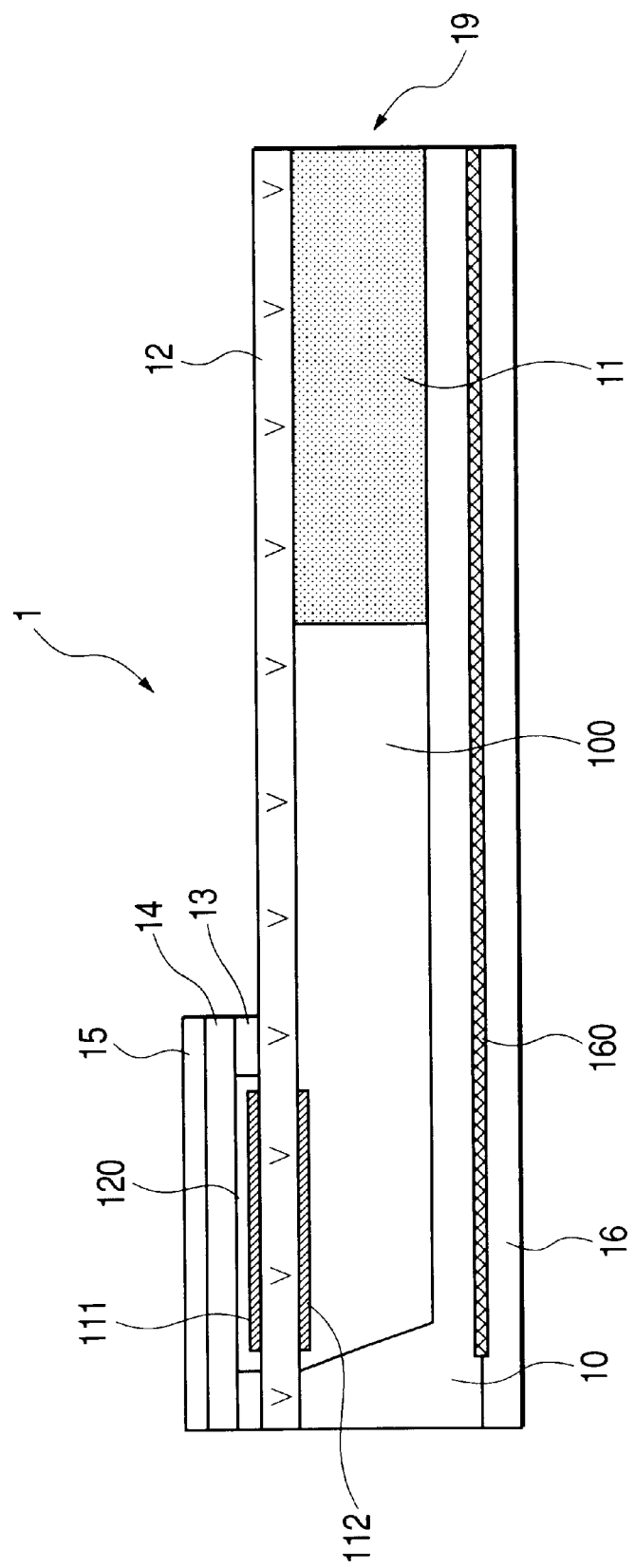
FIG. 1 is a cross-sectional view showing a gas sensing element in accordance with a first embodiment of the present invention.

Preferred embodiments of the present invention will be explained hereinafter with reference to attached drawings. Identical parts are denoted by the same reference numerals throughout the drawings.

First Embodiment

A gas sensing element according to a first embodiment will be explained with reference to FIGS. 1 to 4.

As shown in FIG. 1, a gas sensing element 1 of the first embodiment comprises a solid electrolytic substrate 12. A measured gas side electrode 111 is provided on one surface of the solid electrolytic substrate 12 so as to be exposed to a measured gas. A reference gas side electrode 112 is provided on an opposite surface of the solid electrolytic substrate 12 so as to be exposed to a reference gas stored in a reference gas chamber 100. A water-vapor absorbing member 11 is provided in the vicinity of an opening end 19 of the reference gas chamber 100 so as to substantially close the opening of the reference gas chamber 100.

More specifically, the gas sensing element 1 of this embodiment is incorporated in a gas sensor installed in an exhaust system of an automotive vehicle engine to control the combustion of the engine.

The solid electrolytic substrate 12 is a zirconic member having oxygen ion conductivity. Each of the measured gas side electrode 111 and the reference gas side electrode 112 is platinum.

A diffusion resistive layer 14 is mounted on a measured gas side surface of the solid electrolytic substrate 12 via a spacer 13 so as to define a measured gas chamber 120 surrounding the measured gas side electrode 111. A shielding layer 15 is stacked on the diffusion resistive layer 14 to entirely cover the outer surface of the diffusion resistive layer 14.

All of the spacer 13, the diffusion resistive layer 14, and the shielding layer 15 are alumina. The diffusion resistive layer 14 is a porous member having appropriate gas permeability.

Another spacer 10 is provided on a reference gas side surface of the solid electrolytic substrate 12 so as to define a reference gas chamber 100. A heater substrate 16 is stacked on an opposite surface of the spacer 10. A heating element 160 is sandwiched between the spacer 10 and the heater substrate 16.

The reference gas, i.e., air, is introduced into the reference gas chamber 100 from the opening end 19. An outer end surface of the water-vapor absorbing member 11 and a longitudinal end surface of the gas sensing element 1 are positioned along the same line.

The water-vapor absorbing member 11 is porous alumina and has the porosity of approximately 60%. The water-vapor absorbing member 11 is formed in the inside space of reference gas chamber 100 by alumina dipping.

Although not shown in the drawing, the diffusion resistive layer 14 is bonded on the spacer 13 via an alumina-series adhesive layer. Similarly, the spacer 10 is bonded on the reference gas side surface of the solid electrolytic substrate 12 via an alumina-series adhesive layer.

Hereinafter, the performance of the gas sensing element 1 according to this embodiment will be explained in comparison with a conventional one.

A prepared sample 1 is the above-described gas sensing element 1. A prepared sample 2 is a gas sensing element having the same arrangement as that of the gas sensing element 1 but is modified in that the water-vapor absorbing member 11 is silica gel. Both of the samples 1 and 2 are the samples of this embodiment.

A prepared sample 3 is a conventional sensing element having the same arrangement as that of the gas sensing element 1 except that the water-vapor absorbing member 11 is not provided.

Figure 4:
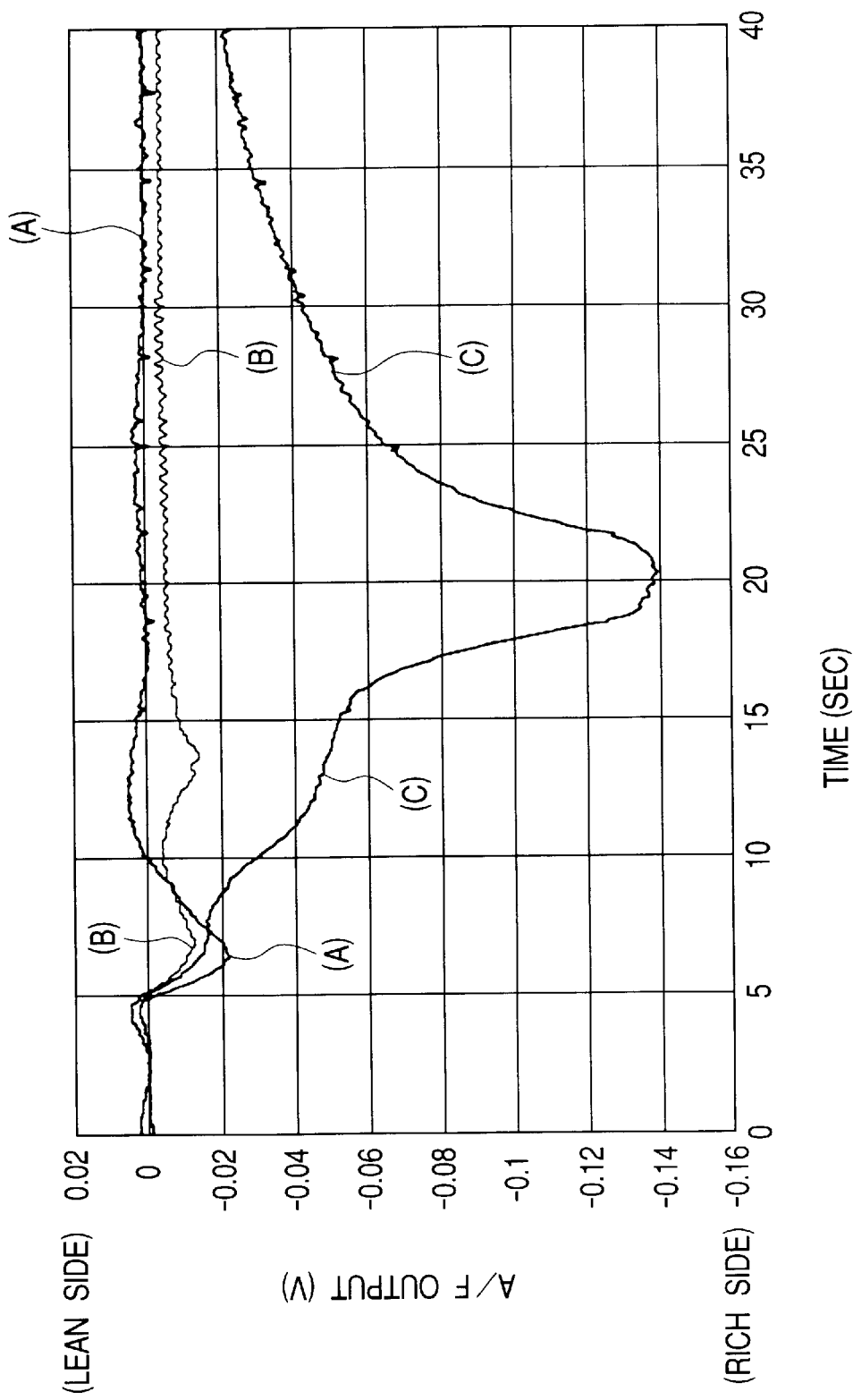
FIG. 4 is a graph showing sensor output characteristics.

These samples 1 to 3 were left in a humid environment (humidity=approximately 60%) at the room temperature for twelve days. Then, each sample was incorporated into a gas sensor (not shown) and installed into a practical engine to measure the sensor output obtained immediately after the engine is started. FIG. 4 shows the measured result, wherein line A is a sensor output of sample 1, line B is a sensor output of sample 2, and line C is a sensor output of sample 3.

In FIG. 4, an abscissa represents an elapsed time since the engine is started, and an ordinate represents an output value (i.e., air-fuel ratio) detected by gas sensing element 1. The sensor output becomes 0 when the detected air-fuel (A/F) ratio is a theoretical value (=14.6). The region larger than 0 is referred to as a lean side, while the region smaller than 0 is referred to as a rich side.

As understood from FIG. 4, the sensor output of sample 3 greatly deviated to the rich side (−0.14 at maximum) from the theoretical value in response to the startup of engine operation because of no presence of water-vapor absorbing member 11. Each of other two samples, i.e., samples 1 and 2, showed a small deviation (−0.02 at maximum) to the rich side.

When the deviation of sensor output to the rich side exceeds −0.02, the engine control system adjusts the air-fuel ratio of the gas mixture introduced into the engine combustion chamber.

According to the samples 1 and 2 of this embodiment, the deviation of sensor output remains within an allowable range. Thus, the engine control system does not operate erroneously.

The gas sensing element 1 of this embodiment has the following functions and effects.

Due to the provision of water-vapor absorbing member 11 in the reference gas chamber 100, the gas sensing element 1 can prevent the water molecules from adhering or settling on the surface of reference gas side electrode 112. Accordingly, it becomes possible to effectively eliminate an abnormal sensor output caused by an oxygen ion current derived from water molecules.

Figure 2:
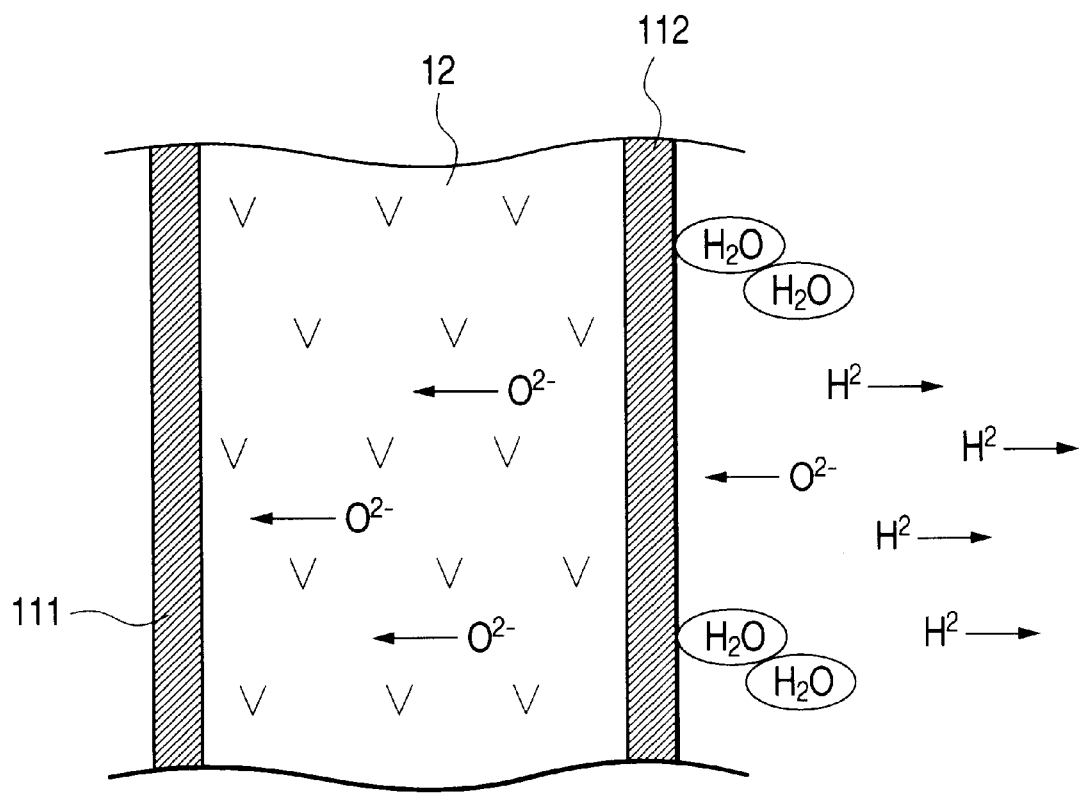
FIG. 2 is an enlarged cross-sectional view showing the generation of oxygen ion current derived from water molecules adhering or settling on a reference gas side electrode in accordance with the first embodiment of the present invention.

Furthermore, as shown in FIG. 2, the supply of heat and the catalytic function of reference gas side electrode 112 cooperatively activate the water molecules adhering on the surface of solid electrolytic substrate 12 and decompose them into oxygen atoms and hydrogen atoms. Oxygen atoms, when ionized, move toward the measured gas side electrode 111 across the solid electrolytic substrate 12 as an oxygen ion current. The oxygen ion current thus produced causes an abnormal sensor output which greatly deviates from the theoretical value to the rich side as shown in FIG. 4.

As described above, the gas sensing element 1 of this embodiment does not produce such an abnormal sensor output. Thus, when the gas sensing element 1 of this embodiment is used to control the combustion of engine, the engine does not stall suddenly due to an abnormal sensor output at the moment the engine operation is started after a long interruption.

In view of the above, this embodiment provides an excellent gas sensing element capable of accurately detecting the oxygen concentration as well as the air-fuel ratio even after the engine is left in an inoperative condition for a long time.

Figure 3:
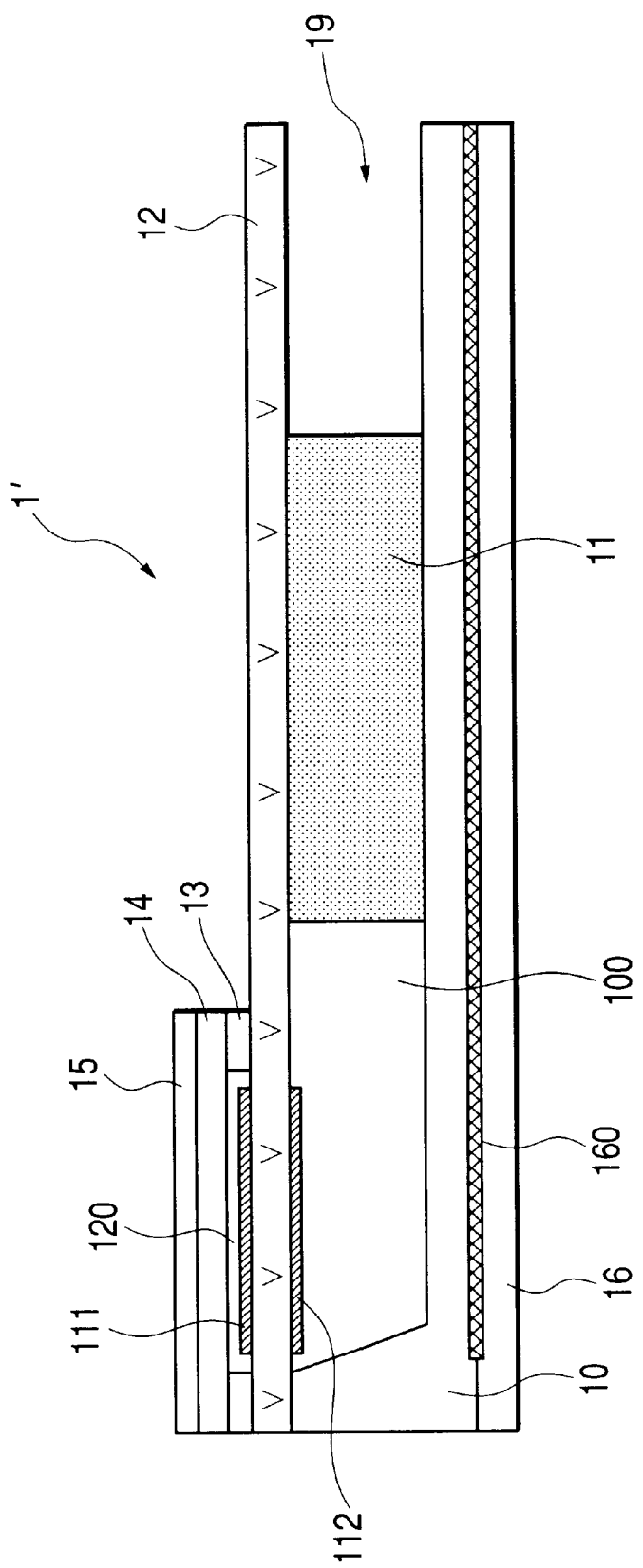
FIG. 3 is a cross-sectional view showing a modified gas sensing element in accordance with the first embodiment of the present invention.

FIG. 3 shows a modified gas sensing element 1' in accordance with the first embodiment of the present invention, which is different in that the water-vapor absorbing member 11 is located at an intermediate (i.e., middle) position in the reference gas chamber 100.

According to this arrangement, the water-vapor absorbing member 11 is offset inward from the opening end 19. It becomes possible to prevent the water-vapor absorbing member 11 from being damaged during an installation of a gas sensor (not shown).

Second Embodiment

Figure 5:
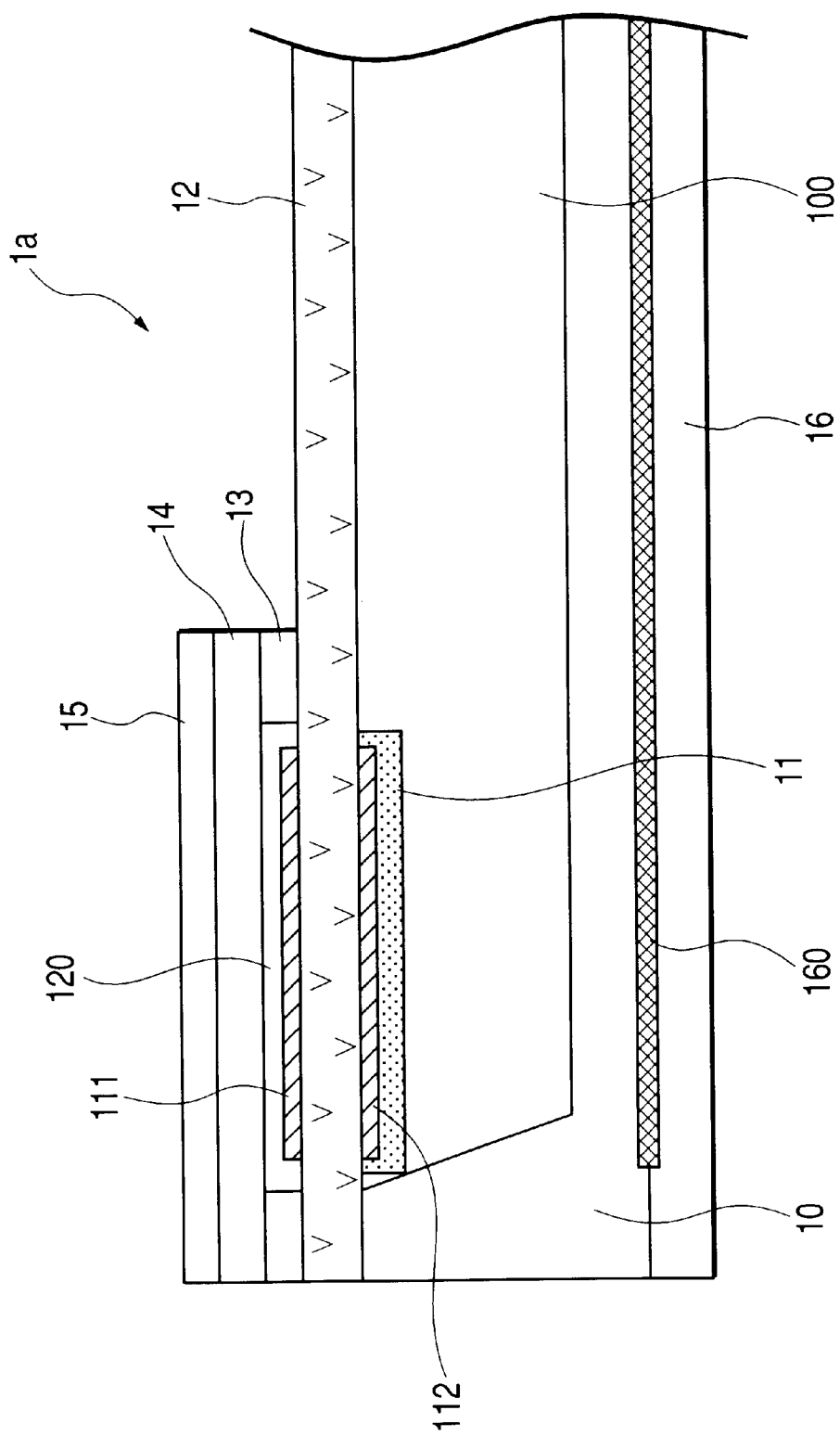
FIG. 5 is a cross-sectional view showing a gas sensing element in accordance with a second embodiment of the present invention.

FIG. 5 shows a gas sensing element 1a in accordance with a second embodiment of the present invention, which is characterized in that the water-vapor absorbing member 11 is provided so as to entirely cover the reference gas electrode 112 provided in the reference gas chamber 100.

The water-vapor absorbing member 11 is an alumina porous member manufactured by dipping.

The rest of the gas sensing element 1a is substantially the same as that of the gas sensing element 1 explained in the first embodiment. Providing this kind of water-vapor absorbing member 11 also makes it possible to provide an excellent gas sensing element capable of surely preventing the water molecules from reaching the reference gas side electrode 112.

In this respect, the gas sensing element 1a of the second embodiment can operate in the same manner as the gas sensing element 1 of the first embodiment.

Third Embodiment

Figure 6:
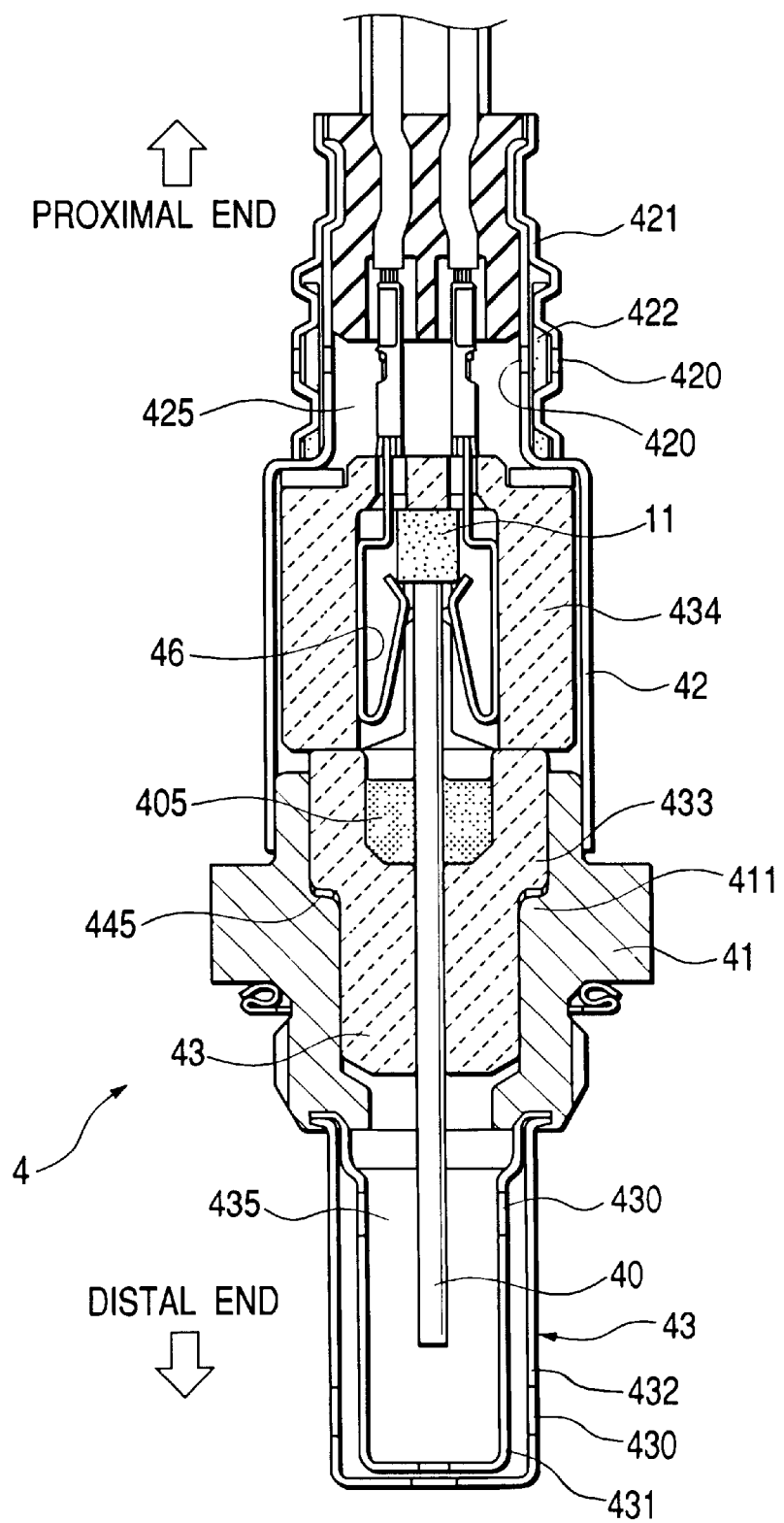
FIG. 6 is a cross-sectional view showing a gas sensor in accordance with a third embodiment of the present invention.

FIG. 6 shows a gas sensor 4 in accordance with a third embodiment of the present invention.

As shown in FIG. 6, the gas sensor 4 of the third embodiment has a cylindrical housing 41 into which a gas sensing element 40 is positioned and securely held. A reference gas side cover 42, provided at a proximal end side of the housing 41, has an air introducing hole 420. A measured gas side cover 43 is provided at a distal end side of the housing 41.

A water-vapor absorbing member 11 is provided in an air introducing passage extending from the air introducing hole 420 to the reference gas chamber (not shown). The gas sensing element 40 has the same arrangement as that of the gas sensing element 1 of the first embodiment except that the water-vapor absorbing member 11 is provided outside the reference gas chamber 100.

More specifically, as shown in FIG. 6, the measured gas side cover 43 has a double-layered structure consisting of an inner cover 431 and an outer cover 432. Both of the inner and outer covers 431 and 432 are provided with a plurality of holes 430 through which the measured gas is introduced into the measured gas side cover 43. In other words, the inner cover 431 confines a measured gas atmosphere 435 surrounding the gas sensing element 40.

The reference gas side cover 42 has a free end (i.e., corresponding to the proximal end of gas sensor 4) overlapped at its outer surface with an outer cover 421. A water-repellent filter 422 is sandwiched between the overlapped portions of the reference gas side cover 42 and the outer cover 421. Both of the reference gas side cover 42 and the outer cover 421 are provided with a plurality of air introducing hole 420 at a predetermined axial position corresponding to the water-repellent filter 422. Therefore, through the air introducing hole 420 and the water-repellent filter 422, the reference gas (i.e., air) is introduced into the reference gas side cover 42. In other words, the reference gas side cover 42 confines a reference gas atmosphere 425.

The housing 41 has a cylindrical inner surface on which a protrusion 411 is provided so as to protrude in the radially inward direction.

The protrusion 411 of housing 41 supports a tapered portion 433 provided on an outer side surface of an insulator 43. A metallic ring packing 445 is interposed between the protrusion 411 of housing 41 and the tapered portion 433 of the insulator 43 so as to airtightly isolate the reference gas atmosphere 425 from the measured gas atmosphere 435.

The gas sensing element 40 is inserted in an axially extending bore of insulator 43. A sealing member 405 airtightly seals the clearance between an inner surface of insulator 43 and the gas sensing element 40.

A reference gas side insulator 434 is disposed axially next to the insulator 43. A total of four leads 46 are disposed in an inside space of the reference gas side insulator 434.

The sensor 4 is equipped with a total of four electrode terminals (not shown) extending outward from the sensor body for two sensor output electrodes and two heater power electrodes. These electrode terminals are connected to the leads 46 in the sensor body.

The reference gas chamber of the gas sensing element 40 is opened to reference gas atmosphere the 425. The water-vapor absorbing member 11 is provided so as to close the opening end of the gas sensing element 40. The water-vapor absorbing member 11 is located between the leads 16 in the inside space of the reference gas side insulator 434. The water-vapor absorbing member 11 is a bulk body of silica gel through which all of the air is introduced into the reference gas chamber.

The gas sensor 4 of this embodiment has the following functions and effects.

According to the gas sensor 4, the air is introduced into the reference gas chamber of the gas sensing element 40 through the air introducing hole 420. The water-vapor absorbing member 11 is provided at the opening end of the gas sensing element 40, i.e., in the air introducing passage. Thus, it becomes possible to prevent the water vapor from entering into the reference gas chamber.

Accordingly, this embodiment prevents the water components from adhering or settling on the reference gas electrode even when the gas sensing element 40 is left in an inoperative condition for a long time. It becomes possible to effectively prevent the abnormal sensor output.

As apparent from the foregoing, the third embodiment provides an excellent gas sensor capable of accurately detecting the oxygen concentration as well as the air-fuel ratio even after the engine is left in an inoperative condition for a long time.

According to this embodiment, it is also preferable to provide a cover member, serving as a water-vapor shielding portion, which is capable of selectively opening or closing the air introducing passage.

The cover member opens the air introducing passage upon starting the operation of the engine and closes the air introducing passage upon stopping the operation of the engine. Regarding an opening/closing mechanism for the cover member, it is possible to utilize a motor, a servo mechanism, an other actuator as well as a bimetal and a shape memory alloy.

This arrangement is advantageous in that no processing to the reference gas chamber is required. In other words, the present invention provides a gas sensor which is easy to manufacture.

Fourth Embodiment

Although not shown, the fourth embodiment relates to a gas sensing element characterized in that an insulating thin film is provided so as to cover a surface of the reference gas side electrode.

The insulating thin film is an alumina thin film with a thickness of 1 nm to 10 nm. Furthermore, the insulating thin film of this embodiment is manufactured by the ALE (atomic layer epitaxial) method.

Namely, aluminum chloride and water are gasified and supplied onto a heated surface of the reference gas side electrode. Both gases react on the heated surface to form a thin film having a thickness equivalent to at least one atomic layer. According to this method, due to their gaseous state, the materials can surely reach the reference gas side electrode located at an inner end of the reference gas chamber. This makes it possible to accurately form an insulating thin film.

The rest of the gas sensing element of this embodiment is substantially the same as that of the gas sensing element 1 explained in the first embodiment although the water-vapor absorbing member is not provided.

As described above, the gas sensing element of this embodiment is provided with an alumina thin film covering the reference gas side electrode.

Accordingly, even if the water molecules adhere or settle on the surface of this gas sensing element, the water molecules are blocked by the alumina insulating layer and cannot reach the reference gas side electrode. Meanwhile, due to its kinetic energy, the oxygen contained in the air can penetrate the alumina layer. Thus, the sensor works properly while effectively eliminates an abnormal sensor output caused by an oxygen ion current derived from water molecules.

Fifth Embodiment

The fifth embodiment of the present invention provides a method for manufacturing a gas sensing element having a very smooth surface of a reference gas side electrode.

Figure 7:
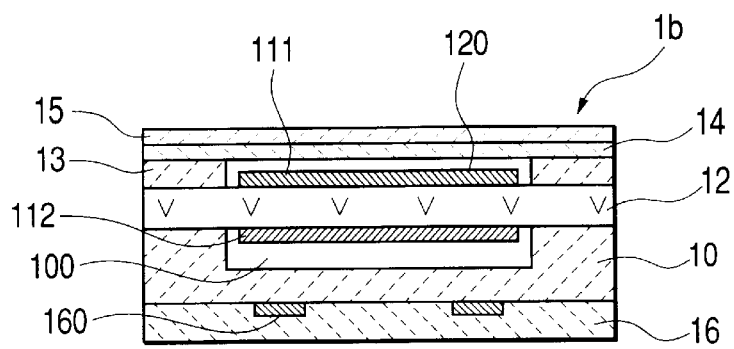
FIG. 7 is a cross-sectional view showing a gas sensing element in accordance with a fifth embodiment of the present invention.
Figure 8:
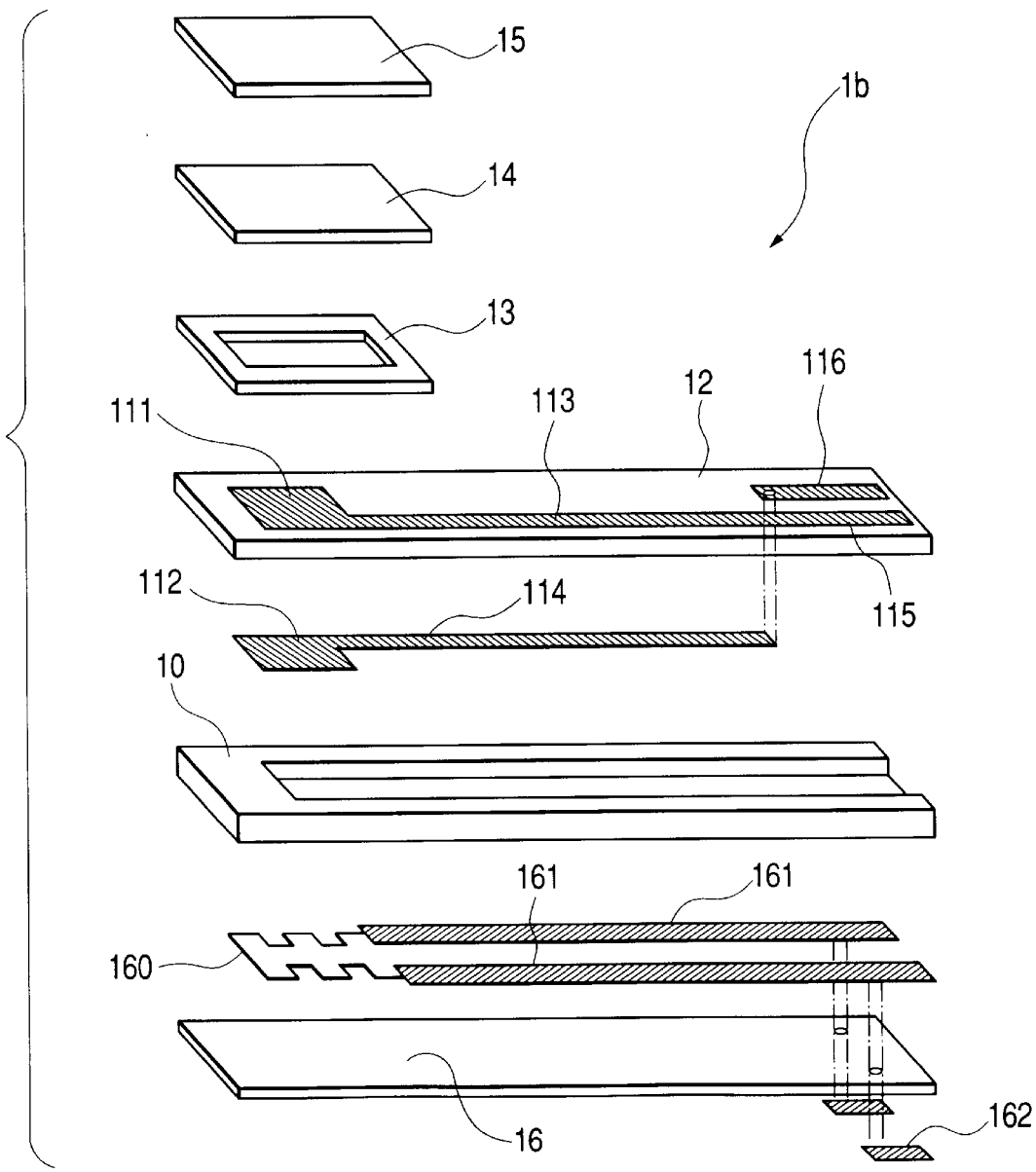
FIG. 8 is a perspective exploded view showing the gas sensing element in accordance with the fifth embodiment of the present invention.

As shown in FIGS. 7 and 8, a gas sensing element 1b of this embodiment comprises a solid electrolytic substrate 12 which is a zirconic member having oxygen ion conductivity, a measured gas side electrode 111 provided on one surface of the solid electrolytic substrate 12, and a reference gas side electrode 112 provided on an opposite surface of the solid electrolytic substrate 12. Each of the measured gas side electrode 111 and the reference gas side electrode 112 is platinum. Leads 113 and 114 are connected to electrodes 111 and 112, respectively. Terminals 115 and 116 are connected to the leads 113 and 114, respectively.

A diffusion resistive layer 14 is mounted on a measured gas side surface of the solid electrolytic substrate 12 via a spacer 13 so as to define a measured gas chamber 120 surrounding the measured gas side electrode 111. A shielding layer 15 is stacked on the diffusion resistive layer 14 to entirely cover the outer surface of the diffusion resistive layer 14.

All of the spacer 13, the diffusion resistive layer 14, and the shielding layer 15 are alumina. The diffusion resistive layer 14 is a porous member having appropriate gas permeability.

Another spacer 10 is provided on a reference gas side surface of the solid electrolytic substrate 12 so as to define a reference gas chamber 100. A heater substrate 16 is stacked on an opposite surface of the spacer 10. A heating element 160 is sandwiched between the spacer 10 and the heater substrate 16. A pair of leads 161 are connected to the heating element 160 to supply electric power to the heating element 160. Terminals 162 are connected to the ends of the leads 161.

The above-described gas sensing element 1b is manufactured in the following manner.

The materials used for forming a green sheet of the solid electrolytic substrate 12 are as follows.

First, 94.0 mol % zirconia and 6.0 mol % yttria are dispensed to obtain a mixed powder. Then, 0.15 weight part of $Si_2$ and 2.0 weight part of $Al_2O_3$ are added to 100 weight part of the mixed powder, and grinded and mixed together in a pot mill for a predetermined time.

Next, the obtained grinded mixture is mixed with an organic solvent (mixed solution of ethanol and toluene), a binder (polyvinyl butyral), and a plasticizing agent (di-butyl phthalate) to obtain a slurry.

Next, the obtained slurry is processed according to the doctor blade method to configure it into a sheet. The obtained sheet is cut into a rectangular shape. A through hole is opened at a predetermined portion on the sheet. The through hole is necessary to guide the lead 114 of reference gas side electrode 112 to the terminal 116 located near the terminal 115 of measured gas side electrode 111.

Then, a Pt paste containing zirconia is applied on the surface of the sheet by screen printing to form the print portions of the measured gas side electrode 111, reference gas side electrode 112, leads 113 and 114, and terminals 115 and 116. Through the above fabrication processes, the zirconia-series green sheet for the solid electrolytic substrate 12 is obtained.

Subsequently, the green sheet for the solid electrolytic substrate 12 is pressed by applying a predetermined pressure thereon. During the pressing operation, the print portions are subjected to the applied pressure.

A green sheet for the heater substrate 16 is fabricated in the following manner.

By using a hot mill, an alumina powder having a predetermined grain size is mixed with an organic solvent (mixed solution of ethanol and toluene), a binder (polyvinyl butyral), and a plasticizing agent (di-butyl phthalate) to obtain a slurry.

Next, the obtained slurry is processed according to the doctor blade method to configure it into a sheet. The obtained sheet is cut into a rectangular shape.

Two through holes are opened at end portions on the sheet. These through holes are necessary to guide the leads 161 of heating element 160.

Then, a Pt paste containing alumina is applied on the surface of the sheet by screen printing to form the print portions of the heating element 160, leads 161, and terminals 162. Through the above fabrication processes, the alumina-series green sheet for the heater substrate 16 is obtained.

Meanwhile, another sheet is fabricated and provide predetermined cutout portions to obtain the spacers 10 and 13.

A green sheet for the diffusion resistive layer 14 is fabricated in the following manner.

By using a hot mill, an alumina powder having a predetermined grain size (larger than that of the alumina-series insulating sheet) is mixed with an organic solvent (mixed solution of ethanol and toluene), a binder (polyvinyl butyral), and a plasticizing agent (di-butyl phthalate) to obtain a slurry.

Next, the obtained slurry is processed according to the doctor blade method to configure it into a sheet. The obtained sheet is cut into a rectangular shape.

A green sheet for the shielding layer 15 is fabricated in the following manner.

A slurry is prepared in the same manner as the heater substrate 16.

Next, the obtained slurry is processed according to the doctor blade method to configure it into a sheet. The obtained sheet is cut into a rectangular shape to obtained the green sheet for the shielding layer 15.

The zirconia-series green sheet and the alumina-series green sheets thus fabricated are stacked in a predetermined order (as shown in FIGS. 7 and 8) and pressed together to obtain a lamination body. The pressed lamination body is then sintered at 1,500° C. for one hour, thereby obtaining the gas sensing element 1b.

According to the observation based on a surface roughness meter, it was confirmed that the reference gas side electrode 112 of the obtained gas sensing element 1b has a surface roughness of 3 μm at maximum. This is smaller than a value (5 μm or above) of a conventional gas sensing element.

In the manufacturing of the gas sensing element manufactured in accordance with this embodiment, the pressing force in the range from 10 MPa to 70 MPa is applied on the solid electrolytic green sheet. This makes it possible to smoothen the surface of the reference gas side electrode 112. Accordingly, water molecules cannot easily adhere or settle on the reference gas side electrode. Thus, it becomes possible to obtain a gas sensing element capable of effectively eliminating an abnormal sensor output caused by an oxygen ion current derived from water molecules.

Sixth Embodiment

The sixth embodiment of the present invention provides another method for manufacturing a gas sensing element having a very smooth surface of reference gas side electrode.

The gas sensing element of this embodiment is manufactured in the same manner as that of the fifth embodiment. However, the manufacturing method of this embodiment is characterized in that the print portion for forming the reference gas side electrode 112 includes 5–10 wt % $ZrO_2$ grains contained in 100 wt % electrode paste.

A pressing force of 5 MPa is applied on the green sheet after the electrode print portions are formed. Although the applied pressure is somewhat lower then that of the fifth embodiment, it is possible to obtain a gas sensing element having a smooth electrode surface equivalent to that of the fifth embodiment.

Accordingly, in forming the print part of the reference gas side electrode, using the above-described electrode paste makes it possible to effectively reduce the surface roughness of the reference gas side electrode without being adversely influenced by the inclusion of $ZrO_2$ grains. The surface of the reference gas side electrode becomes so smooth that molecules cannot easily adhere or settle on the reference gas side electrode. It becomes possible to obtain a gas sensing element capable of effectively eliminating an abnormal sensor output caused by an oxygen ion current derived from water molecules.

Seventh Embodiment

Figure 9:
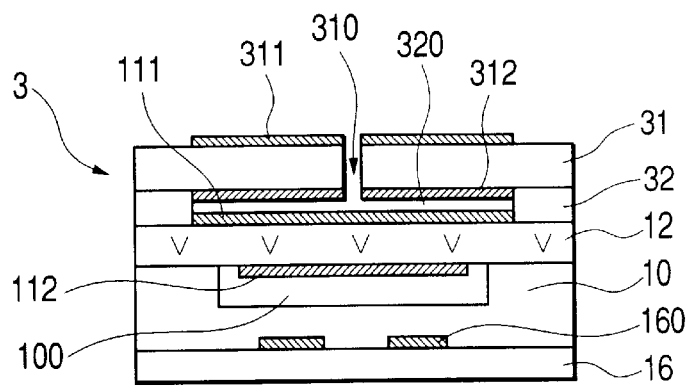
FIG. 9 is a cross-sectional view showing a gas sensing element in accordance with a seventh embodiment of the present invention.
Figure 10:
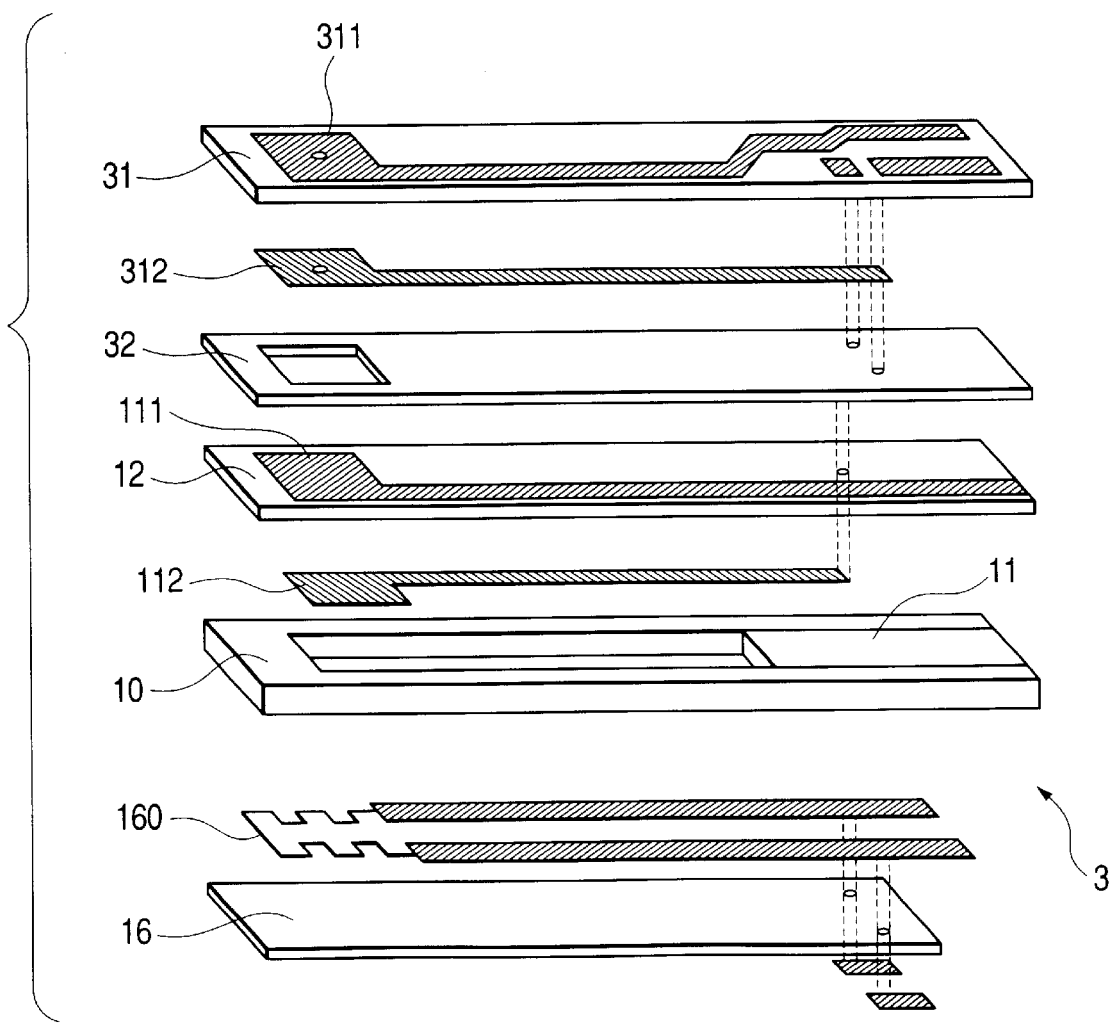
FIG. 10 is a perspective exploded view showing the gas sensing element in accordance with the seventh embodiment of the present invention.

FIGS. 9 and 10 show a 2-cell type gas sensing element 3 in accordance with the seventh embodiment of the present invention.

The gas sensing element 3 comprises two zirconia-series solid electrolytic sheets 12 and 31, two spacers 10 and 32, and a heater substrate 16. A pair of pump electrode 311 and 312 is provided on opposite surfaces of the solid electrolytic sheet 31. A pin hole 310, introducing a measured gas into a measured gas chamber 320, is provided so as to extend from the one pump electrode 311 to the other pump electrode 312 across the solid electrolytic sheet 31. A heating element 160 is provided on the surface of the heater substrate 16. The measured gas chamber 320 is defined by the spacer 32. The measured gas chamber 320 forms a measured gas atmosphere surrounding a measured gas side electrode 111.

The rest of the arrangement of this embodiment is substantially the same as that of the first embodiment.

The gas sensing element 3 of this embodiment has the capability of measuring a wide range of air-fuel ratio and therefore makes it possible to realize an accurate air-fuel ratio control of an automotive vehicle engine.

This invention may be embodied in several forms without departing from the spirit of essential characteristics thereof. The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A gas sensing element comprising:
    a solid electrolytic substrate;
    a measured gas side electrode provided on one surface of said solid electrolytic substrate so as to be exposed to a measured gas; and
    a reference gas side electrode provided on an opposite surface of said solid electrolytic substrate so as to be exposed to a reference gas stored in a reference gas chamber; and
    an insulating thin film is provided on a surface of said reference gas side electrode, whereby water molecules are blocked from adhering or settling on the electrode surface and cannot reach the reference gas side electrode,
    wherein a thickness of said insulating thin film is in a range from 1 nm to 10 nm.

* * * * *